US012623017B2

(12) United States Patent
Scott et al.

(10) Patent No.: US 12,623,017 B2
(45) Date of Patent: May 12, 2026

(54) ACTIVATION MECHANISM FOR AN ON-BODY MEDICAMENT DELIVERY DEVICE

(71) Applicant: SHL MEDICAL AG, Zug (CH)

(72) Inventors: Daniel Scott, Deerfield Beach, FL (US); Slobodan Stefanov, Deerfield Beach, FL (US)

(73) Assignee: SHL Medical AG, Zug (CH)

( * ) Notice: Subject to any disclaimer, the term of this patent is extended or adjusted under 35 U.S.C. 154(b) by 1088 days.

(21) Appl. No.: 17/602,879

(22) PCT Filed: Apr. 8, 2020

(86) PCT No.: PCT/EP2020/059964
§ 371 (c)(1),
(2) Date: Oct. 11, 2021

(87) PCT Pub. No.: WO2020/216617
PCT Pub. Date: Oct. 29, 2020

(65) Prior Publication Data
US 2022/0160960 A1 May 26, 2022

Related U.S. Application Data

(60) Provisional application No. 62/836,754, filed on Apr. 22, 2019.

(30) Foreign Application Priority Data

May 2, 2019 (EP) .................................... 19172201

(51) Int. Cl.
*A61M 5/158* (2006.01)
(52) U.S. Cl.
CPC ..... *A61M 5/158* (2013.01); *A61M 2005/1585* (2013.01); *A61M 2005/1586* (2013.01)

(58) Field of Classification Search
CPC .......... A61M 5/158; A61M 2005/1585; A61M 2005/1586; A61M 2005/14252;
(Continued)

(56) References Cited

U.S. PATENT DOCUMENTS

| | | | | |
|---|---|---|---|---|
| 2014/0005950 A1* | 1/2014 | Groeschke | .............. | G16Z 99/00 |
| | | | | 702/19 |
| 2019/0091404 A1 | 3/2019 | Nazzaro et al. | | |
| 2021/0196892 A1* | 7/2021 | Dasbach | ................. | A61M 5/50 |

FOREIGN PATENT DOCUMENTS

| | | |
|---|---|---|
| JP | 2016-521171 A | 7/2016 |
| KR | 2014-0089547 A | 7/2014 |

(Continued)

OTHER PUBLICATIONS

International Search Report and Written Opinion for Int. App. No. PCT/EP2020/059964, mailed Aug. 13, 2020.

*Primary Examiner* — Kami A Bosworth
*Assistant Examiner* — Avery Smale
(74) *Attorney, Agent, or Firm* — McDonnell Boehnen Hulbert & Berghoff LLP

(57) ABSTRACT

An activation mechanism for an on-body medicament delivery device, wherein the activation mechanism comprises: an activation button structure configured to be moved between an initial position and an activation position, an activation pin sleeve, and a biased activation pin received by the activation pin sleeve, the activation pin being configured to be linearly movable from an initial retracted position relative to the activation pin sleeve to an extended position towards which the activation pin is biased, the activation button structure being configured to interact with the activation pin sleeve in the initial position to cause the activation pin sleeve to engage with and maintain the activation pin in the retracted position, and wherein the activation button structure is configured to interact with the activation pin sleeve (Continued)

when the activation button structure is moved linearly towards the activation position causing the activation pin sleeve to release the activation pin from the retracted position.

20 Claims, 8 Drawing Sheets

(58) Field of Classification Search
CPC .... A61M 2005/30588; A61M 5/14248; A61M 2205/6036; A61M 2005/31588
See application file for complete search history.

(56) References Cited

FOREIGN PATENT DOCUMENTS

| WO | 2014/179776 A1 | 11/2014 |
| WO | 2017/007952 A1 | 1/2017 |
| WO | 2017/205816 A1 | 11/2017 |
| WO | 2018060025 A1 | 4/2018 |
| WO | 2019/032384 A1 | 2/2019 |

* cited by examiner

ACTIVATION MECHANISM FOR AN ON-BODY MEDICAMENT DELIVERY DEVICE

CROSS REFERENCE TO RELATED APPLICATIONS

The present application is a U.S. National Phase Application pursuant to 35 U.S.C. § 371 of International Application No. PCT/EP2020/059964 filed Apr. 8, 2020, which claims priority to U.S. Provisional Patent Application No. 62/836,754 filed Apr. 22, 2019 and European Patent Application No. 19172201.6, filed May 2, 2019. The entire disclosure contents of these applications are herewith incorporated by reference into the present application.

TECHNICAL FIELD

The present disclosure generally relates to medicament deliver devices, in particular to on-body medicament delivery devices.

BACKGROUND

On-body medicament delivery devices, or wearable medicament delivery devices, is a category of devices that are worn by the user. On-body medicament delivery devices are hence configured to be fixed to the body of a user. They may for example be used when medicament administration should be performed over a timeframe that is longer than what an auto-injector or manual injector can provide. An on-body medicament delivery device may for example be configured to provide continuous medicament delivery for one or more hours.

Since on-body medicament devices are worn by the user, the injection delivery member is typically contained within the on-body medicament delivery device before the injection sequence is commenced. The injection delivery member is typically inserted into the injection site after the user has triggered the injection sequence.

WO2019/032384 A1 discloses a wearable injector which includes a housing, and an injection needle translatable along a needle axis between a retracted position in which the tip of the injection needle is contained within the injector housing, and an injection position in which the tip protrudes from the injector housing. An activation button structure is movably mounted to the injector housing and operatively connected to the injection needle. The activation button structure is translatable along a button axis, parallel to the needle axis, from an unactuated position to an actuated position which is visually different than the unactuated position. A biasing member is connected with the activation button structure and the injection needle. The biasing member is stabilized in a stored energy state in the unactuated position of the activation button structure and released in the actuated position of the activation button structure into an energy releasing state to drive the injection needle along the needle axis from the retracted position to the injection position.

The configuration disclosed in WO2019/032384 A1 requires a design in which the needle is arranged is essentially arranged axially aligned with the button axis. Additionally, the design requires the depression of a biased button, which needs a high activation force.

SUMMARY

An object of the present disclosure is to provide an activation mechanism for an on-body medicament delivery device which solves or at least mitigates problems of the prior art.

There is hence provided an activation mechanism for an on-body medicament delivery device, wherein the activation mechanism comprises: an activation button structure configured to be moved between an initial position and an activation position, an activation pin sleeve, and a biased activation pin received by the activation pin sleeve, the activation pin being configured to be linearly movable from an initial retracted position relative to the activation pin sleeve to an extended position towards which the activation pin is biased, the activation button structure being configured to interact with the activation pin sleeve in the initial position to cause the activation pin sleeve to engage with and maintain the activation pin in the retracted position, and wherein the activation button structure is configured to interact with the activation pin sleeve when the activation button structure is moved linearly towards the activation position causing the activation pin sleeve to release the activation pin from the retracted position.

The pin sleeve can hence be translated along a longitudinal axis of the activation pin sleeve. This provides a freedom of design with regards to the location of the delivery member, e.g. a metal needle and/or a soft cannula.

The activation button structure may be configured to be moved linearly between the initial position and the activation position.

One embodiment comprises a biased delivery member mechanism, including a delivery member, which delivery member mechanism is in a locked position, in which the delivery member is in an initial delivery member position, when the activation pin is in the retracted position, wherein the activation pin is configured to release the delivery member mechanism from the locked position when the activation pin is moved towards the extended position to thereby move the delivery member linearly from the initial delivery member position to an administration position.

The activation pin hence triggers movement of the delivery member, when released from its initial engagement with the activation pin sleeve.

According to one embodiment the delivery member mechanism includes a needle and a soft cannula, the soft cannula being configured to receive the needle and move with the needle from the initial delivery member position to the administration position.

According to one embodiment the activation mechanism comprises a guide structure and the delivery member mechanism includes a movable structure connected to a delivery member, the movable structure being configured to move in the guide structure together with the delivery member, from the initial delivery member position to the administration position, wherein the movable structure is configured to engage with the guide structure in the administration position, to retain the delivery member in the administration position.

The movable structure may for example comprises a stop, e.g. a ledge, a flexible arm, a recess or a cut-out configured to engage with the guide structure in the administration position of the delivery member/guide structure.

According to one embodiment the delivery member comprises a needle and a soft cannula.

According to one embodiment the activation mechanism comprises a guide structure and the delivery member mechanism comprises a movable structure configured to move in the guide structure, the movable structure including a first member and a second member which is movable relative to the first member, wherein the first member is fixedly connected to a needle and the second member is connected to a soft cannula connected to the needle, the first member and the second member being configured to move with the needle and the soft cannula from the initial delivery member position to the administration position, wherein the second member is configured to engage with the guide structure to retain the soft cannula in the administration position, wherein the first part is allowed to move back whereby the needle moves back to the initial delivery member position with the first member.

According to one embodiment the delivery member mechanism includes a torsionally biased first delivery member actuator and a linearly movable locking member configured to prevent rotation of the first delivery member actuator when the activation pin is in the retracted position whereby the delivery member mechanism is in the locked position, wherein the activation pin is configured to move the locking member and thereby release the first delivery member actuator when the activation pin is moved towards the extended position, causing the first delivery member actuator to rotate, whereby the delivery member mechanism is released from the locked position.

According to one embodiment the delivery member mechanism includes a torsionally biased second delivery member actuator connected to the delivery member, wherein the first delivery member actuator is configured to apply a force onto the second delivery member actuator when the first delivery member actuator is rotated, thereby causing movement of the second delivery member actuator and movement of the delivery member to the administration position.

According to one embodiment the second delivery member actuator is a delivery member actuating torsion spring having a leg connected to the delivery member, and wherein the first delivery member actuator is configured to apply the force onto the leg when the first delivery member actuator is rotated.

According to one embodiment the second delivery member actuator forms a cam mechanism with the first delivery member actuator.

According to one embodiment the delivery member mechanism comprises a drum containing a drum torsion spring, wherein the first delivery member actuator is a drum insert body arranged in the drum, torsionally biased by the drum torsion spring, wherein the drum insert body comprises a protrusion extending axially from the drum, the protrusion being configured to interact with the second delivery member actuator when the first delivery member actuator is rotated.

According to one embodiment the first delivery member actuator is provided with a radial blocking protrusion configured to bear against the locking member in the retracted position of the activation pin to thereby prevent rotation of the first delivery member actuator.

According to one embodiment the drum is provided with an axial slit in which the blocking member is configured to run when moved by the activation pin.

According to one embodiment the activation button structure comprises an activation button and an activation button sleeve fixedly connected to the activation button, wherein the activation button sleeve is configured to receive the activation pin sleeve, wherein the activation pin sleeve is provided with radially inwards extending flexible arms configured to engage with the activation pin, wherein the activation button sleeve is configured to force the radially inwards extending flexible arms radially inwards to engage with the activation pin when the activation button structure is in the initial position, and wherein the activation button sleeve is configured to move axially relative to the activation pin sleeve when the activation button structure is moved towards the activation position enabling the radially inwards flexible arms to flex radially outwards thereby releasing the activation pin from engagement with the activation pin sleeve.

According to one embodiment the activation pin has an electrically conducting surface.

There is according to a second aspect of the present disclosure provided an on-body medicament delivery device comprising: an outer housing, and an activation mechanism according to the first aspect arranged in the housing.

One embodiment comprises at least one electronic component and two contact elements that are spaced apart, wherein the electrically conducting surface of the activation pin is configured to provide an electrical connection between the two contact elements when the activation pin is in the extended position.

One embodiment comprises an inner housing provided with a first seal, wherein the activation pin is configured to pierce the first seal when the activation pin is moved from the retracted position towards the extended position. The inner housing may thereby be kept sterile until the on-body medicament delivery device is being activated.

The on-body medicament delivery device may be an on-body injector, e.g. an on-body auto-injector.

Generally, all terms used in the claims are to be interpreted according to their ordinary meaning in the technical field, unless explicitly defined otherwise herein. All references to "a/an/the element, apparatus, component, means, etc. are to be interpreted openly as referring to at least one instance of the element, apparatus, component, means, etc.", unless explicitly stated otherwise.

BRIEF DESCRIPTION OF THE DRAWINGS

The specific embodiments of the inventive concept will now be described, by way of example, with reference to the accompanying drawings, in which.

DETAILED DESCRIPTION

The inventive concept will now be described more fully hereinafter with reference to the accompanying drawings, in which exemplifying embodiments are shown. The inventive concept may, however, be embodied in many different forms and should not be construed as limited to the embodiments set forth herein; rather, these embodiments are provided by way of example so that this disclosure will be thorough and complete, and will fully convey the scope of the inventive concept to those skilled in the art. Like numbers refer to like elements throughout the description.

Figure 1:
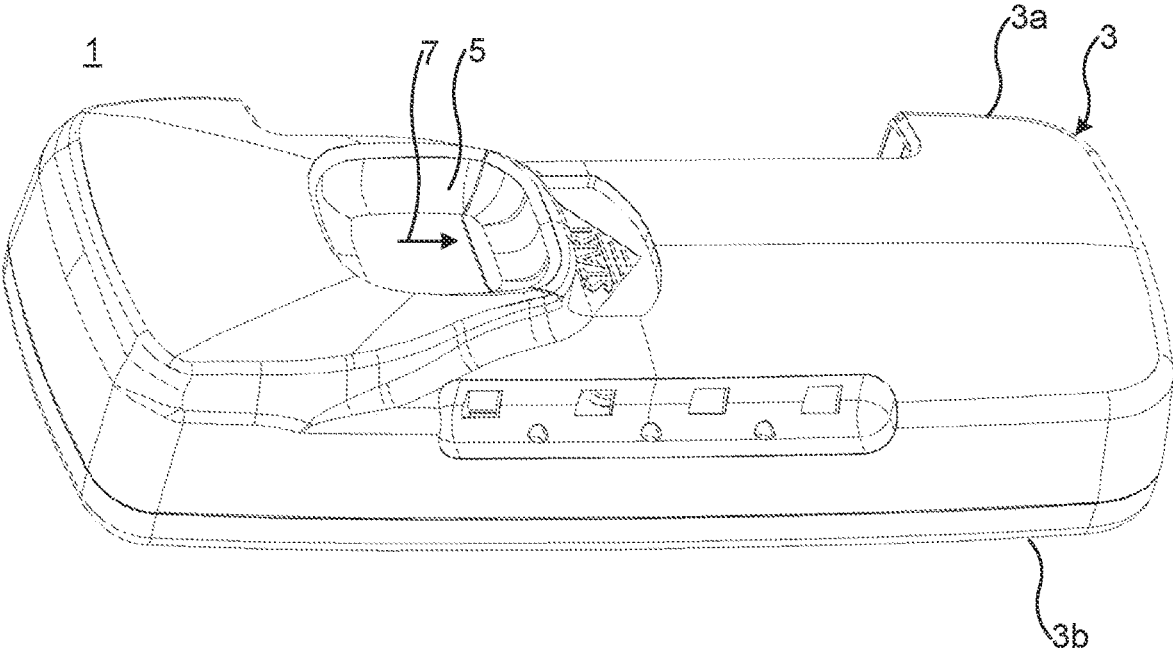
FIG. 1 is a perspective view of an example of an on-body medicament delivery device.

FIG. 1 shows an example of an on-body medicament delivery device 1. The exemplified on-body medicament delivery device 1 is an auto-injector. The exemplified on-body medicament delivery device 1 may be a single use/disposable medicament delivery device.

The on-body medicament delivery device 1 has an external or outer housing 3. The outer housing 3 comprises an upper housing part 3a and a lower housing part 3b. The upper housing part 3a and the lower housing part 3b may be configured to be assembled with each other.

The lower housing part 3b is configured to face the user's body and the injection site when the on-body medicament delivery device 1 is worn by a user. The on-body medicament delivery device 1 may for example be glued to a user's body by means of an adhesive layer provided on the lower housing part 3b or by any other means that is known in the art.

The on-body medicament delivery device 1 comprises an activation button 5. The activation button 5 is configured to be moved relative to the outer housing 3. The on-body medicament delivery device 1 can thereby be activated. Medicament expulsion may hence be initiated. The exemplified activation button 5 is slidable relative to the outer housing 3. The activation button 5 is slidable in the direction shown by arrow 7.

Figure 2:
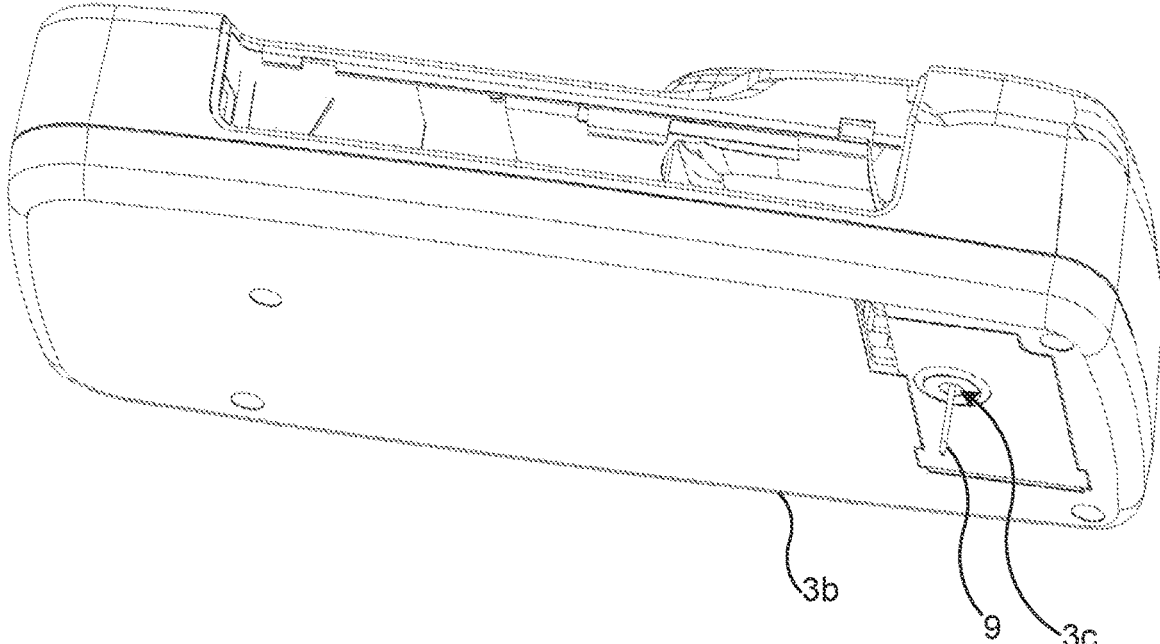
FIG. 2 is a perspective view of a bottom face of the on-body medicament delivery device in FIG. 1.

FIG. 2 shows a view of the lower housing part 3b of the on-body medicament delivery device 1. The lower housing part 3b has a medicament member through-opening 3c through which a delivery member 9 may extend. In the present example, the delivery member 9 may be a needle or a needle provided with a soft cannula. The delivery member 9 is in FIG. 2 in an administration position in which it extends from the lower housing part 3b. The administration position is achieved by activating the on-body medicament delivery device 1 by means of the activation button 5 as will be described in detail herein. Prior to activation, the delivery member is in an initial delivery member position, in which it is retracted relative to the outer housing 3 and arranged fully inside the outer housing 3.

Figure 3:
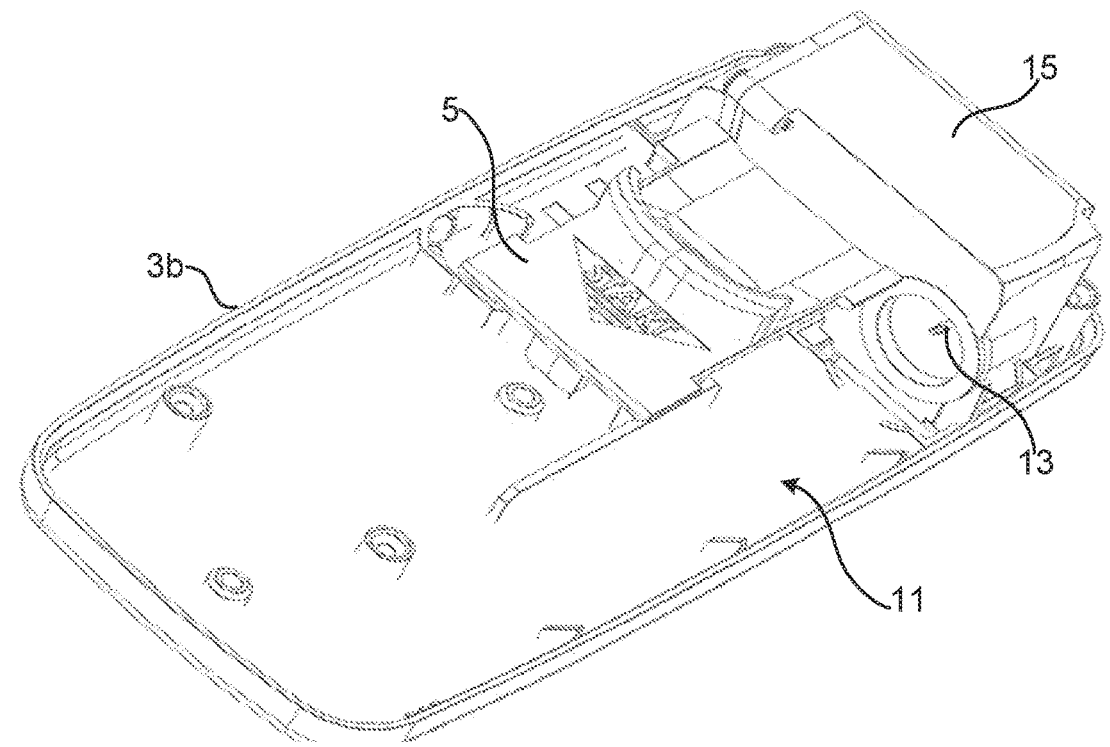
FIG. 3 is a perspective view of the on-body medicament delivery device with its outer housing removed.

FIG. 3 shows the on-body medicament delivery device 1 from another view, with the upper housing part 3a removed to expose the interior of the on-body medicament delivery device 1. The exemplified on-body medicament delivery device 1 has a medicament container holding area 11 where a medicament container is configured to be arranged. The on-body medicament delivery device 1 furthermore comprises a first inner pipe 13 configured to be connected to the medicament container and to the delivery member 9. Medicament from the medicament container may thereby be expelled from the on-body medicament delivery device 1 via the delivery member 9.

The on-body medicament delivery device 1 furthermore comprises an inner housing 15, which contains a delivery member mechanism. Alternatively, the on-body medicament delivery device 1 could be provided without the inner housing 15. The inner housing 15 may for example be provided for improved sterility.

Figure 4:
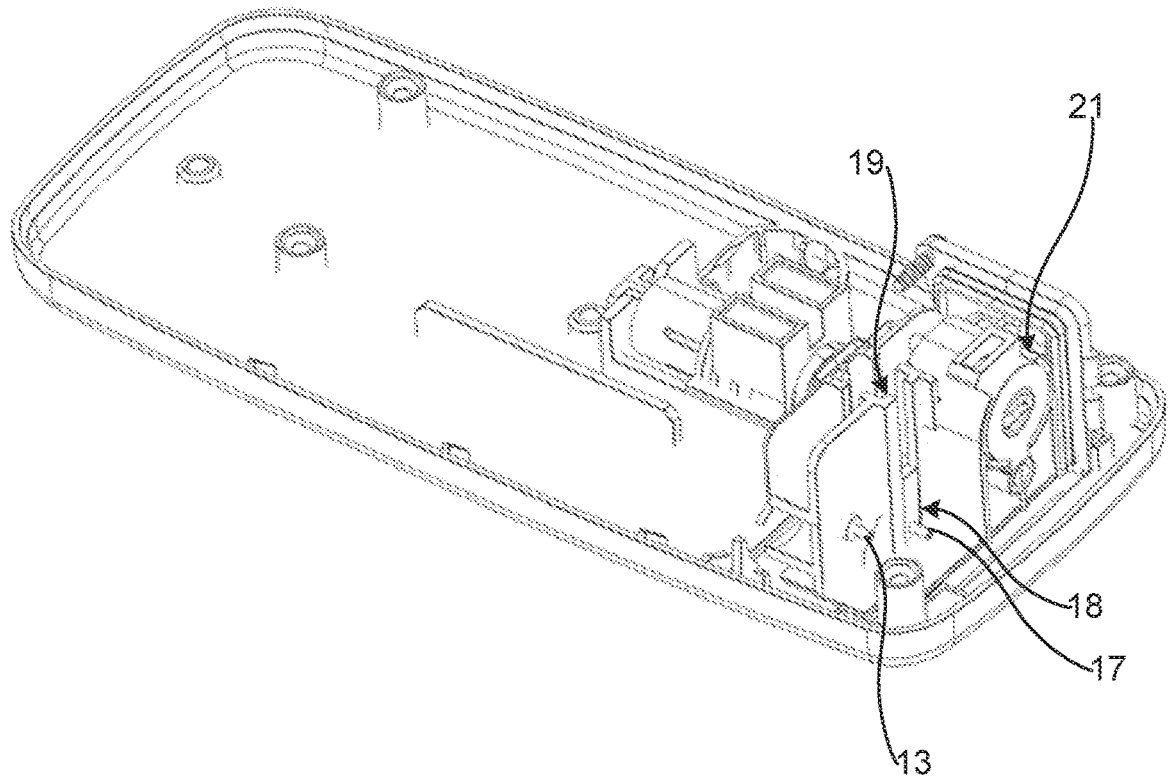
FIG. 4 is another perspective view with an inner housing removed.

FIG. 4 shows the on-body medicament delivery device 1 with the upper housing part 3a and the inner housing 15 removed. The activation button 5 has also been removed.

The on-body medicament delivery device 1 comprises a movable structure 18 which comprises the second inner pipe 17 and the delivery member 9, and a flexible tube (not shown).

The flexible tube connects the first inner pipe 13 and the second inner pipe 17. The second inner pipe 17 is connected to the delivery member 9. The delivery member 9 is arranged essentially perpendicular to the second inner pipe 17 to be able to penetrate the medicament member through-opening 3c.

The on-body medicament delivery device 1 comprises a guide structure 19 configured to guide movement of the movable structure 18. The guide structure 19 comprises a track in which the movable structure 18 is configured to run/move from an initial position in which the delivery member is in the initial delivery member position, and a second position in which the delivery member is in the administration position.

FIG. 4 furthermore shows the delivery member mechanism 21.

Figure 5:
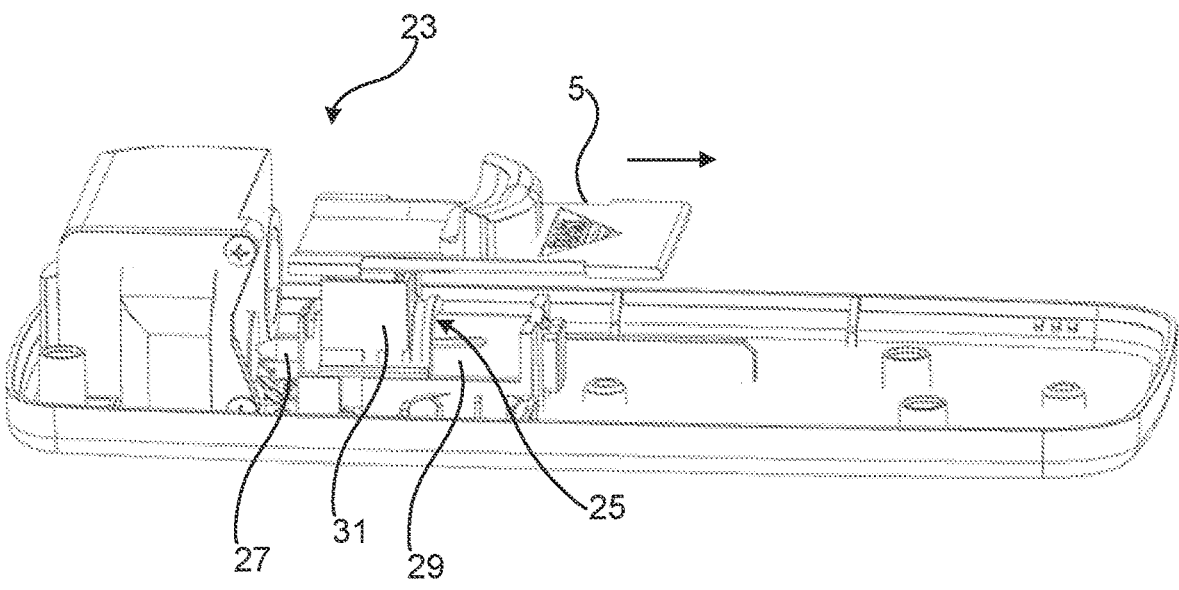
FIG. 5 is another perspective view of the on-body medicament delivery device 1 with the outer housing removed.

FIG. 5 depicts the on-body medicament delivery device 1 in perspective from the side with the upper housing part 3a removed. The on-body medicament delivery device 1 comprises an activation mechanism 23. The activation mechanism 23 comprises an activation structure 25, an activation pin 27, and an activation pin sleeve 29. The activation structure 25 comprises the activation button 5 and an activation button sleeve 31.

Figure 6:
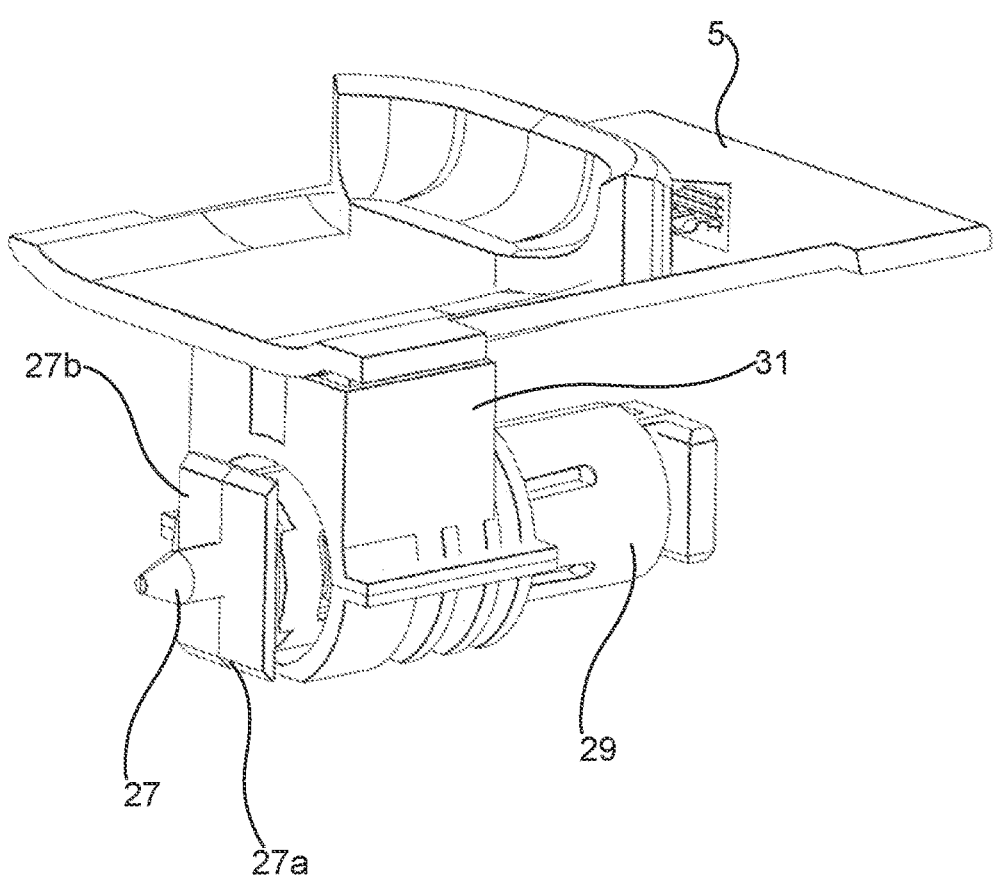
FIG. 6 shows an example of a part of an activation mechanism of the on-body medicament delivery device in FIG. 1.

FIG. 6 shows the activation mechanism 23 with the activation button 5, the activation button sleeve 31, the activation pin 27, and the activation pin sleeve 29. The activation button 5 and the activation button sleeve 31 are in the present example provided as two separate parts with the activation button 5 mechanically connected to the activation button sleeve 31 in a fixed manner relative to each other, but they could alternatively be formed of an integral structure.

The activation button sleeve 31 is configured to receive the activation pin sleeve 29. The activation pin sleeve 29 is configured to receive the activation pin 27. In FIG. 6, the activation button structure 25, and hence the activation button 5 and the activation button sleeve 31, is in an initial position relative to the activation pin sleeve 29. The activation structure 25, and hence the activation button 5 and the activation button sleeve 31, are movable to an activation position relative to the activation pin sleeve 29.

The activation pin sleeve 29 is configured to engage with the activation pin 27 when the activation button structure 25 is in the initial position. The activation pin sleeve 29 is configured to disengage from the activation pin 27 when the activation button structure 25 is moved towards the activation position. The activation pin 27 is in a retracted position relative to the activation pin sleeve 29 when the activation button structure 25 is in the initial position. The activation pin 27 is configured to move towards an extended position when the activation pin sleeve 29 releases the activation pin 27. The activation pin 27 is biased towards its extended position.

The on-body medicament delivery device 1 may comprise a resilient member (not shown), such as a spring, configured to bias the activation pin 27 towards the extended position.

The activation pin 27 may have an electrically conducting surface 27a. The activation pin 27 may have a protruding structure 27b, which extends radially relative to the longitudinal axis of the activation pin 27. The electrically conducting surface 27a may form part of the perimeter of the protruding structure 27b. The electrically conducting surface 27a may for example form part of the perimeter closest to the inner surface of the lower housing part 3b.

Figures 7, 8:
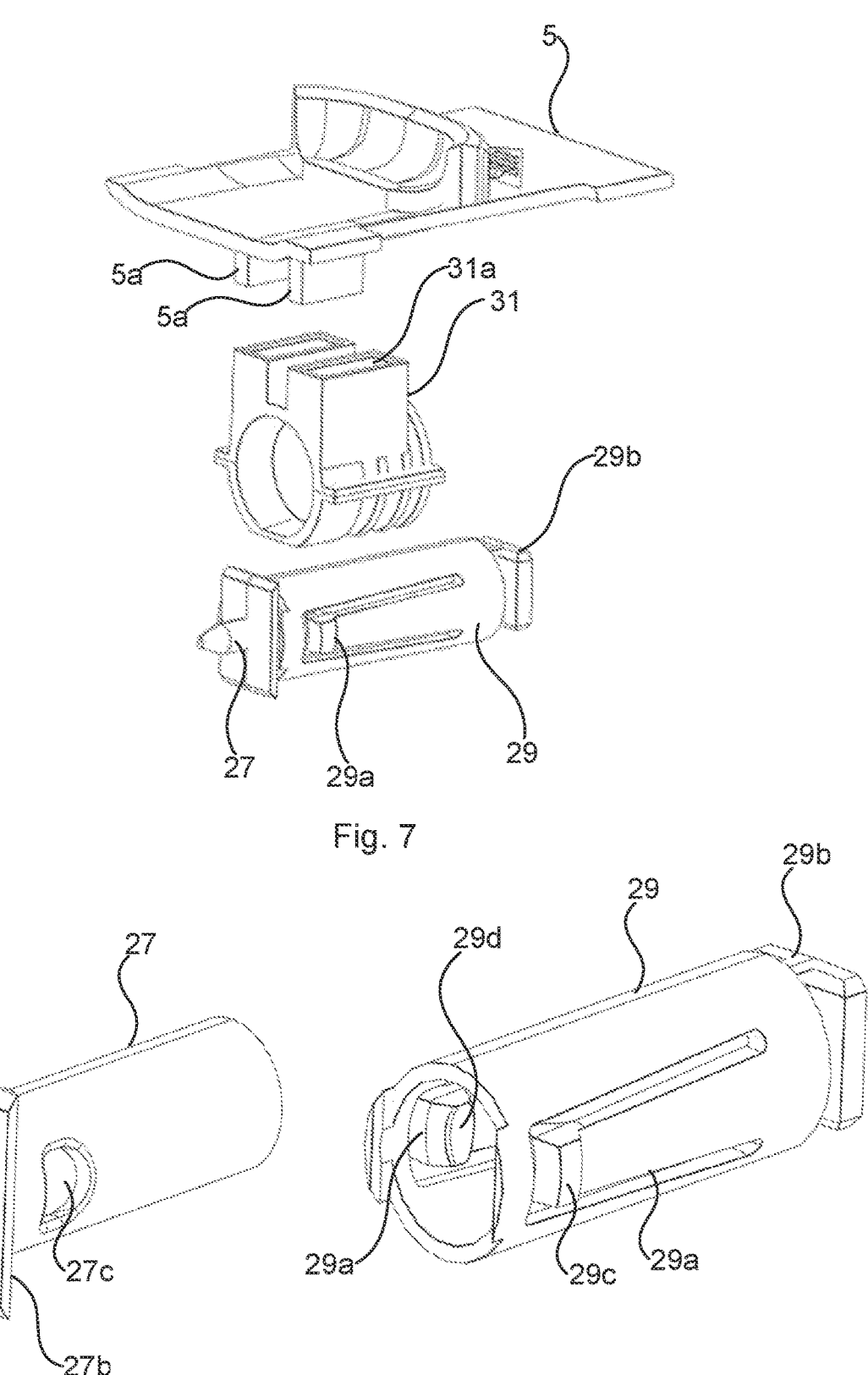
FIG. 7 shows part of an activation mechanism of the on-body medicament delivery device in FIG. 1.
FIG. 8 shows an example of an activation pin and an activation pin sleeve.

FIG. 7 shows the activation mechanism 23 in FIG. 6 with the activation button sleeve 31 removed from the activation pin sleeve 29. According to the example shown in FIG. 7, the activation button 5 has protrusions 5a configured to engage with corresponding recesses 31a of the activation button sleeve 31. The activation button 5 and the activation button sleeve 31 are thereby fixedly engaged.

The activation pin sleeve 29 has an engagement structure 29b configured to engage with the outer housing 3. The engagement structure 29b is according to the present example configured to engage with the lower housing structure 3b. The activation pin sleeve 29 is configured to be fixed relative to the outer housing 3. The activation pin sleeve 29 is configured to be fixed relative to the lower housing structure 3b. The resilient member may be arranged inside the activation pin 27, bearing against the engagement structure 29b to thereby bias the activation pin 27 towards the extended position.

The activation pin sleeve 29 is provided with radially inwards extending flexible arms 29a. Only one radially inwards extending flexible arm 29a is visible in FIG. 7.

FIG. 8 shows the activation pin 27 removed from activation pin sleeve 29. The activation pin 27 is provided with recesses 27c configured to receive a respective one of the radially inwards extending flexible arms 29a. The activation pin sleeve 29 thereby engages with the activation pin 27. The radially inwards extending flexible arms 29a are pressed radially inwards by the inner surface of the activation button sleeve 31, when the activation button structure 25 is in the initial position. The radially inwards extending flexible arms 29a are in this state not able to move out from the recesses 27c. The activation pin 27 is hence maintained in the retracted position. When the activation button structure 25, including the activation button sleeve 31 is moved towards the activation position, the activation button sleeve 31 moves axially relative to the activation pin sleeve 29. The activation button sleeve 31 moves away from the radially inwards extending flexible arms 29a, enabling the radially inwards extending flexible arms 29a to move radially outwards out from the recesses 27c. The radially inwards extending flexible arms 29a may be provided with outer protrusions 29c configured to interact with the inner surface of the activation button sleeve 31. The radially inwards extending flexible arms 29a may be provided with inner protrusions 29d configured to interact and engage with a respective recess 27c.

Figure 9:
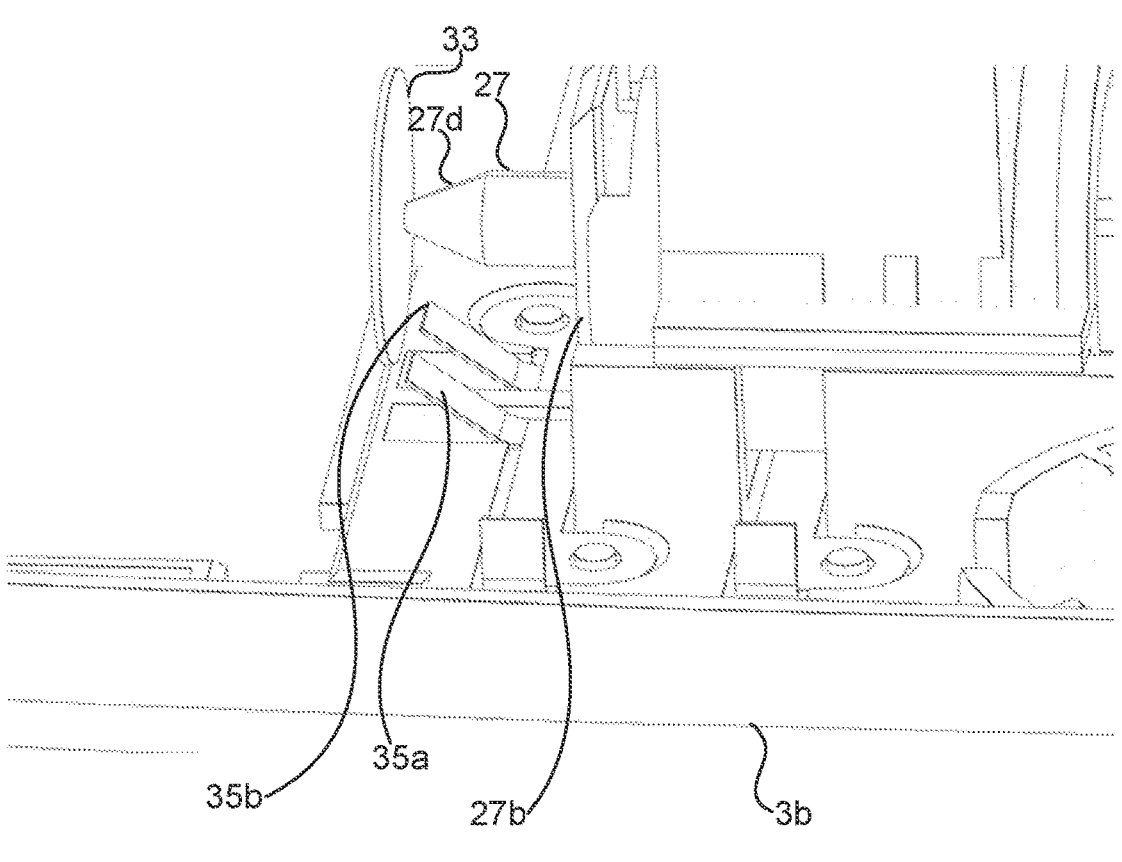
FIG. 9 shows a close-up view of the activation pin and electrodes.

FIG. 9 shows a close-up view of the activation pin 27, with the entire inner housing and its contents removed for clarity. The on-body medicament delivery device 1 may comprise a first seal 33. The first seal 33 is configured to seal the inner housing 15. The activation pin 27 is configured to pierce the first seal 33 when the activation pin 27 is moved from the retracted position towards the extended position.

The activation pin 27 may have a tapering head 27d to facilitate the piercing of the first seal 33.

The on-body medicament delivery device 1 may also comprise one or more electronic components, such as an electric motor to drive a plunger rod into the medicament container, and or processing circuitry, communications circuitry, light indicators or the like. The on-body medicament delivery device 1 may comprise contact elements, or first and second electrodes 35a and 35b. When the first and second electrodes 35a and 35b are electrically connected they close an electric circuit to drive the one or more electronic components. The first and second electrodes 35a and 35b are not electrically connected to each other when the activation pin 27 is in the retracted position. The electric circuit is hence open. The activation pin 27 is configured to contact the first and the second electrode 35a and 35b when the activation pin 27 is moved from the retracted position towards the extended position. In particular, the electrically conducting surface 27a is configured to contact the first electrode 35a and the second electrode 35b simultaneously. The first electrode 35a and the second electrode 35b are hence short-circuited and the electric circuit is closed. The one or more electronic components of the on-body medicament delivery device 1 are thereby activated.

Figure 10:
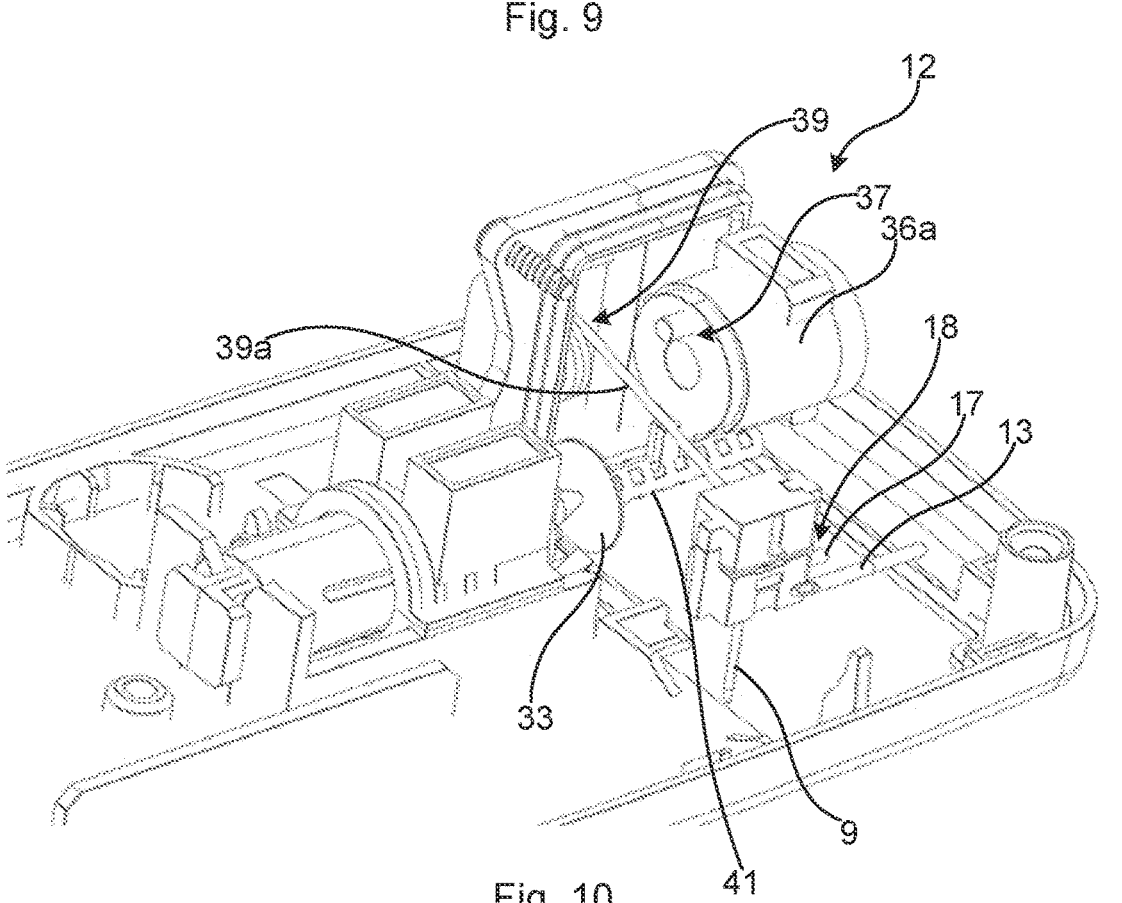
FIG. 10 shows an example of a delivery member mechanism in a locked position.

FIG. 10 shows the delivery member mechanism 21. The structure and operation of the delivery member mechanism 21 will be described in the following. The delivery member mechanism 21 may form part of the activation mechanism 23. The delivery member mechanism 21 is in a locked position when the activation pin 27 is in the retracted position. The delivery member 9 is in this case in the initial delivery member position completely contained inside the outer housing 3. The activation pin 27 is configured to release the delivery member mechanism 21 from the locked position when moved from the retracted position towards the extended position, causing the delivery member 9 to move from the initial delivery member position towards the administration position.

The exemplified delivery member mechanism 23 comprises a torsionally biased first delivery member actuator 37. The first delivery member actuator 37 is configured to be rotatable. The delivery member mechanism 23 comprises a linearly movable locking member 41, which is configured to prevent the first delivery member actuator 37 to rotate when the activation pin 27 is in the retracted position. When the activation pin 27 is moved towards the extended position, it moves the locking member 41. The locking member 41 is thereby moved from a position in which it prevents the first delivery member actuator 37 from rotation to a position in which the first delivery member actuator 37 is set free to rotate.

The delivery member mechanism 23 comprises a torsionally biased second delivery member actuator 39. The second delivery member actuator 39 is a delivery member actuation torsion spring. The delivery member actuation torsion spring has a leg 39a. The second delivery member actuator 39 is connected to the delivery member 9 via the movable structure 18. The leg 39a may be connected to the delivery member 9 via the movable structure 18. The first delivery member actuator 37 is configured to apply a force onto the second delivery member actuator 39 when the first delivery member actuator 37 is being rotated and impacts with or presses against the leg 39a. This causes movement of the second delivery member actuator 39, in particular of the leg 39a, which thereby moves the movable structure 18 and the delivery member 9 linearly from the initial delivery member position to the administration position. The first delivery member actuator 37 and the second delivery member actuator 39 hence form a sort of cam mechanism.

Figure 11:
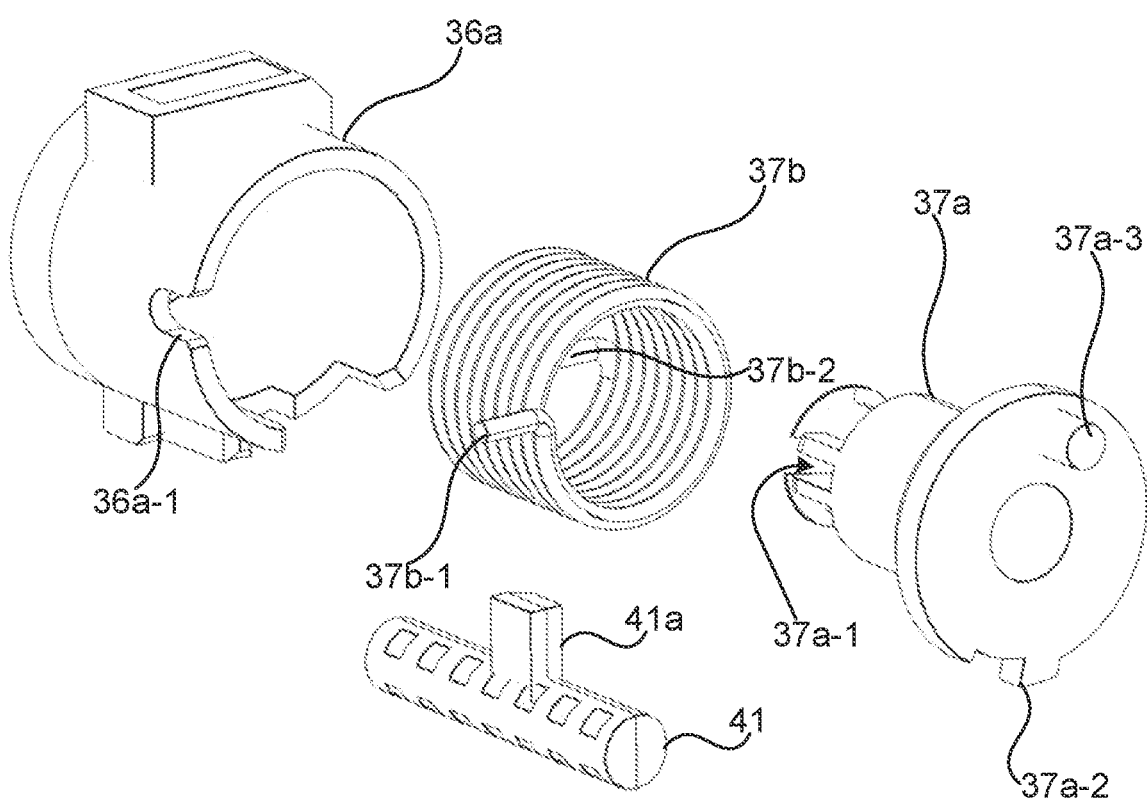
FIG. 11 shows a part of the delivery member mechanism.

The delivery member mechanism 23 comprises a drum 36*a* which is fixedly arranged in the inner housing 15. The first delivery member actuator 27 has a drum insert body 37*a* configured to be received by the drum 36*a*. These components are shown in more detail in FIG. 11. The delivery member mechanism 23 also comprises a drum torsion spring 36*b*. The drum torsion spring 36*b* is configured to be arranged in the drum 36*a*. The drum torsion spring 36*b* is configured to torsionally bias the drum insert body 37*a*. The drum torsion spring 36*b* is configured to be fixed to the drum 36*a*. The drum torsion spring 36*b* is also configured to be fixed to the drum insert body 37*a*. The drum 36*a* has a drum recess 36*a*-1 configured to receive a first end portion 36*b*-1 of the drum torsion spring 36*b*. The drum insert body 37*a* has a drum insert body recess 37*a*-1 configured to receive a second end portion 36*b*-2 of the drum torsion spring 36*b*. The drum insert body 37*a* has a protrusion 37*a*-3. The protrusion 37*a*-3 extends axially from the drum insert body 37*a* parallel with the central axis of the drum insert body 37*a*.

The drum 36 may further comprise a rotation stop, configured to interact with a counter rotation stop on the first delivery member actuator 37 (not shown).

The drum insert body 37*a* has a radial blocking protrusion 37*a*-2. This could alternatively be a radial recess. The locking member 41 has a locking member protrusion 41*a* configured to engage with or bear against the radial blocking protrusion 41*a* when the activation pin 27 is in the retracted position. The locking member 41 hence prevents rotation of the torsionally biased drum insert body 37*a* when the activator pin 27 is in the retracted position. This situation is shown in FIG. 10, where the drum insert body 37*a* is torsionally biased to rotate clockwise but prevented from doing so by the locking member 41, which bears against the radial blocking protrusion 37*a*-2.

Figure 12:
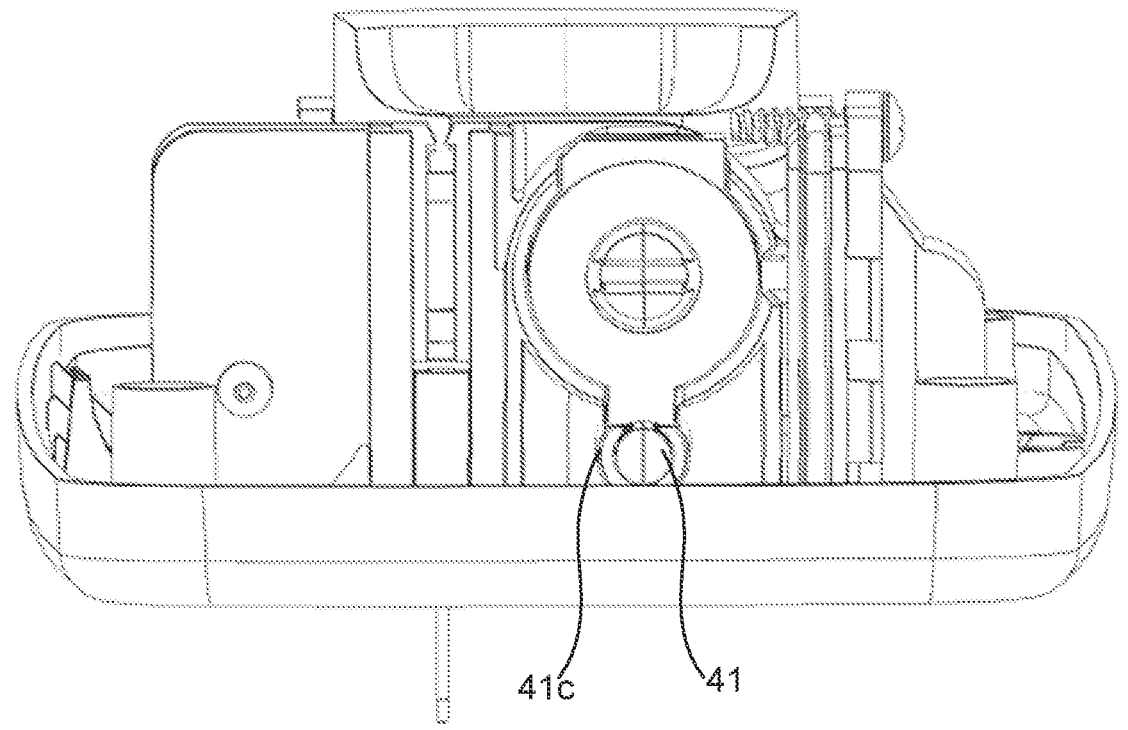
FIG. 12 shows a short end face of the on-body medicament delivery device with the outer housing removed.

The locking member 41 is configured to slide in a locking member channel 41*b*, shown in FIG. 12. The locking member channel 41*b* may for example be provided in a holding structure configured to hold the drum 36*a*. The drum 36*a* may be provided with a slit to enable the radial blocking protrusion 41*a* to run along the drum 36*a*.

Figure 13:
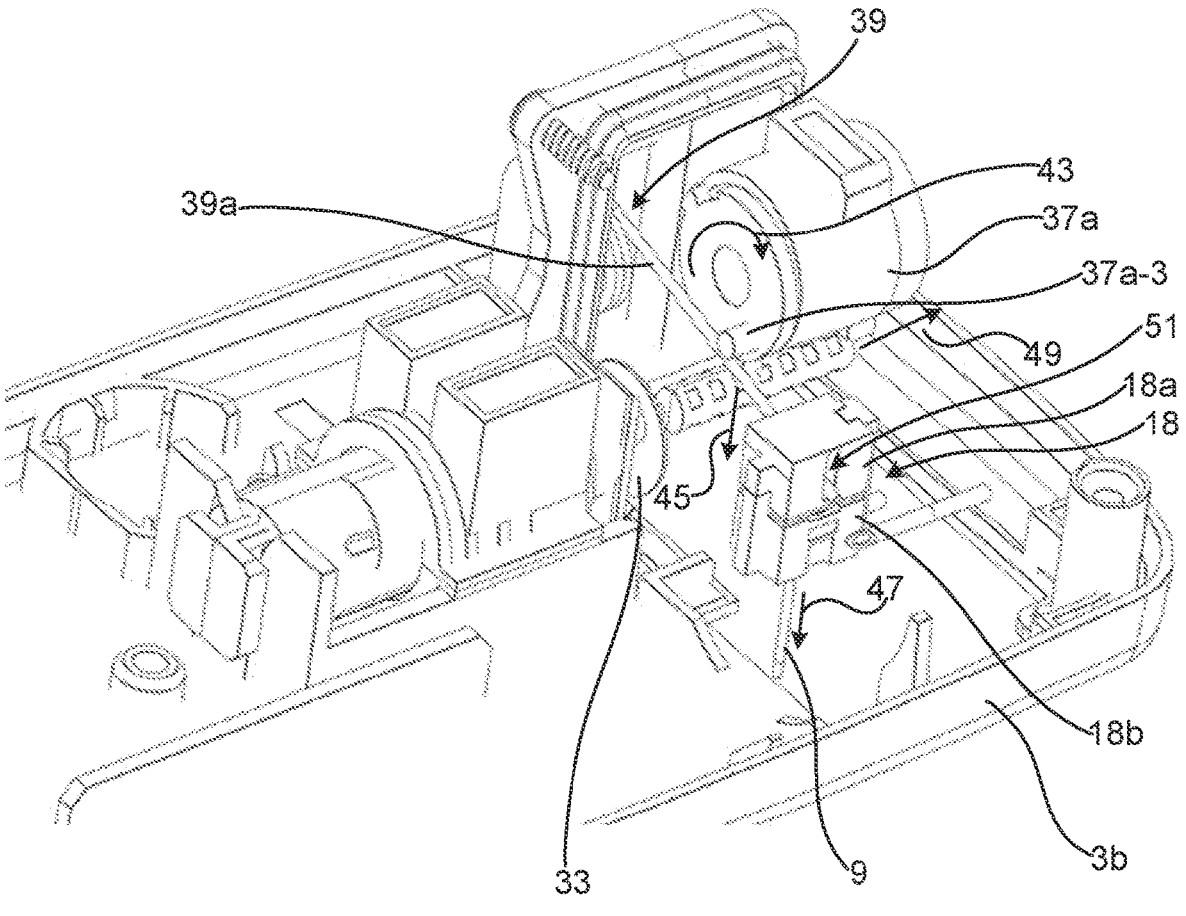
FIG. 13 shows the delivery member mechanism in FIG. 10 when it has been released from the locked position.

In FIG. 13 the first delivery member actuator 37, and in particular the drum insert body 37*a* has been rotated as shown by arrow 43, applying a force in the direction shown by arrow 45 onto the leg 39*a*, causing movement of the second delivery member actuator 39 and linear movement of the delivery member 9 as shown by arrow 47. To obtain the state shown in FIG. 13, a user has moved the activation button 5 from the initial position to the activation position. This has caused the release of the activation pin 27, which has pierced the first seal 33 and resulted in translation of the locking member 41, causing the locking member protrusion 41*a* to move past the radial blocking protrusion 37*a*-2. The drum insert body 37*a* has thereby been rotated clockwise. The protrusion 37*a*-3 has impacted with the leg 39*a*, which is connected to the delivery member 9, causing the delivery member 9 to penetrate a second seal (not shown) as it moves out from the lower housing part 3*b* and obtain the administration position. It is to be noted that the end of the leg 39*a* has not moved in relation to the situation shown in FIG. 10 and this is due to an incorrect drawing of the position of the leg 39*a* in FIG. 10, which should be vertically higher. The end of the leg 39*a* may be arranged in a guide member 51 which is configured to run in the guide structure 19.

FIG. 13 further shows an example of the movable structure 18, which includes a first member 18*a* and a second member 18*b*, movable relative to the first member 18*a*. The first member 18*a* is in the example an upper member and the second member 18*b* is a lower member, positioned closer to the lower housing part 3*b* than the first member 18*a*. The second inner pipe 17 is connected to the second member 18*b*. The delivery member 9 includes a needle which is fixedly connected to the first member 18*a*. The delivery member 9 also includes a soft cannula which is arranged around the needle. The soft cannula is arranged fixed to the second member 18*b*. The soft cannula is connected to the second inner pipe 17. The leg 39*a* is configured to actuate the first member 18*a*. When the leg 39*a* is pressed downwards by the protrusion 37*a*-3, the first member 18*a* is moved towards the lower housing part 3*b*. The second member 18*b* is moved towards the lower housing part 3*b* by the first member 18*a*. The needle with the soft cannula arranged around it is therefore moved towards the administration position. The second member 18*b* is configured to engage with the guide structure 19 when the needle attains the administration position, for example by means of a snap-engagement. The second member 18*b* is thereby locked in this position, and the soft cannula is locked in the administration position. The drum insert body 37*a* may leave the leg 39*a*, but the soft cannula will be left in the administration position and stay in the user's body. When the leg 39*a* is moved back to its initial position, the first member 18*a* to which the leg 39*a* is connected will thereby move back to its initial position. The needle, which is fixed to the first member 18*a* will then leave the user's body while the soft cannula is maintained therein.

According to a variation of the above, the movable member could instead be made of a single piece. In this case, the delivery member may comprise a needle but no soft cannula.

Figure 14:
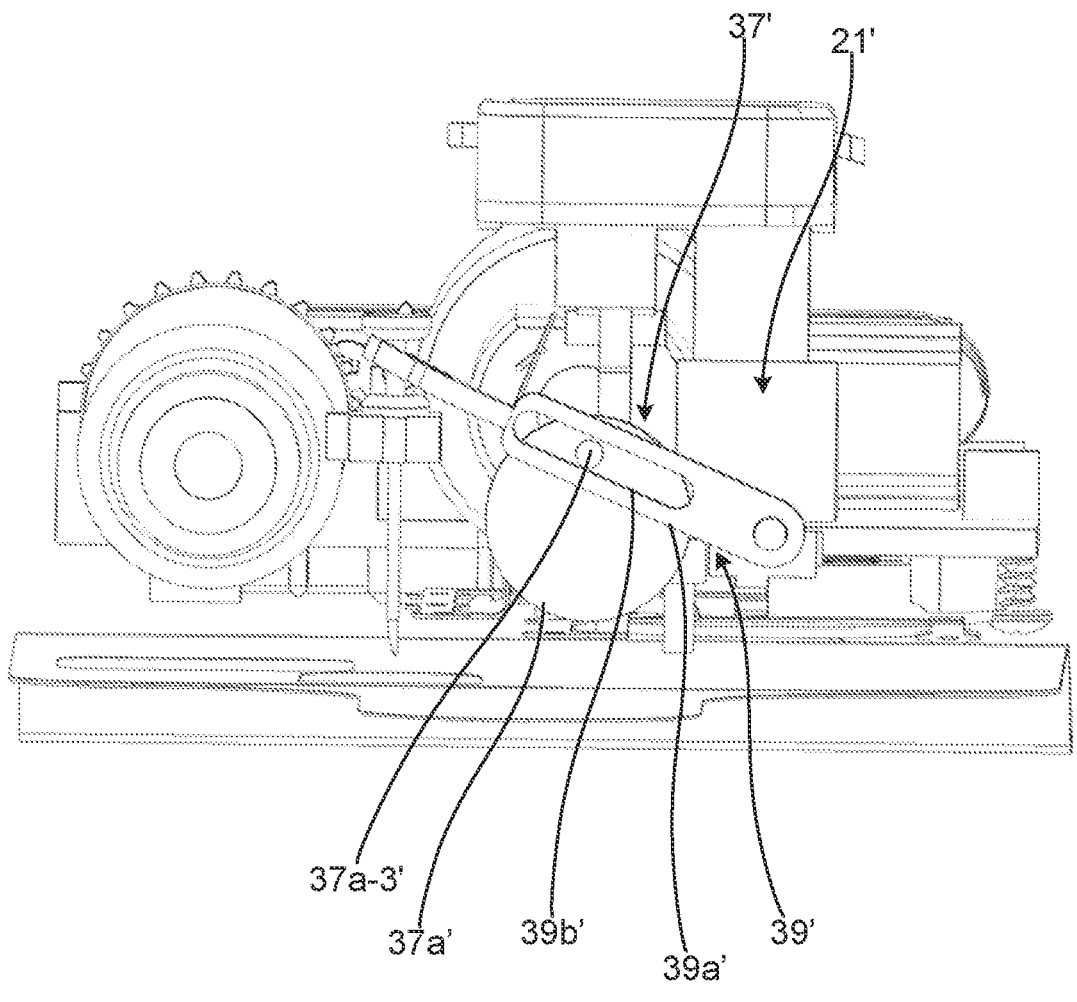
FIG. 14 shows an alternative example of the delivery member mechanism.

FIG. 14 shows another example of the delivery member mechanism 21. The exemplified delivery member mechanism 21' has a first delivery member actuator 37' similar to the first delivery member actuator 37, comprising a rotatable drum insert body 37*a*'. The drum insert body 37*a*' has the protrusion 37*a*-3'. The delivery member mechanism 21' has a second delivery member actuator 39', which comprises a pivoted lever 39*a*' and forms a cam mechanism with the first delivery member actuator 37'. The lever 39*a*' has a slit 39*b*' configured to receive the protrusion 37*a*-3'. The drum insert body 37*a*' is configured to rotate when the activation pin is moved towards the extended position, similarly as has been described above. Rotation of the drum insert body 37*a*' causes the protrusion 37*a*-*d*' to slide in the slit 39*b*', causing the lever 39*a*' to pivot. The delivery member is thereby moved from the initial delivery member position towards the administration position.

The inventive concept has mainly been described above with reference to a few examples. However, as is readily appreciated by a person skilled in the art, other embodiments than the ones disclosed above are equally possible within the scope of the inventive concept, as defined by the appended claims.

The invention claimed is:

1. An activation mechanism for an on-body medicament delivery device, wherein the activation mechanism comprises:

an activation button structure configured to be moved between an initial position and an activation position, an activation pin sleeve, and a biased activation pin received by the activation pin sleeve, the activation pin being configured to be linearly movable from a retracted position relative to the activation pin sleeve to an extended position towards which the activation pin is biased, the activation button structure being configured to interact with the activation pin sleeve in the initial position to cause the activation pin sleeve to engage with and maintain the activation pin in the retracted position, and wherein the activation button structure is configured to interact with the activation pin sleeve when the activation button structure is moved linearly towards the activation position causing the activation pin sleeve to disengage from the activation pin and release the activation pin from the retracted position.

2. The activation mechanism as claimed in claim 1, further comprising a biased delivery member mechanism which includes a delivery member, wherein when the delivery member mechanism is in a locked position, the delivery member is in an initial delivery member position, and the activation pin is in the retracted position, the activation pin is configured to be moved towards the extended position to release the delivery member mechanism from the locked position and thereby move the delivery member linearly from the initial delivery member position to an administration position.

3. The activation mechanism as claimed in claim 2, wherein the delivery member mechanism includes a torsionally biased first delivery member actuator and a linearly movable locking member configured to prevent rotation of the first delivery member actuator when the activation pin is in the retracted position whereby the delivery member mechanism is in the locked position, wherein the activation pin is configured to move the locking member and thereby release the first delivery member actuator when the activation pin is moved towards the extended position, causing the first delivery member actuator to rotate, whereby the delivery member mechanism is released from the locked position.

4. The activation mechanism as claimed in claim 3, wherein the delivery member mechanism includes a torsionally biased second delivery member actuator connected to the delivery member, wherein the first delivery member actuator is configured to apply a force onto the second delivery member actuator when the first delivery member actuator is rotated, thereby causing movement of the second delivery member actuator and movement of the delivery member to the administration position.

5. The activation mechanism as claimed in claim 4, wherein the second delivery member actuator is a delivery member actuating torsion spring having a leg connected to the delivery member, and wherein the first delivery member actuator is configured to apply the force onto the leg when the first delivery member actuator is rotated.

6. The activation mechanism as claimed in claim 4, wherein the second delivery member actuator forms a cam mechanism with the first delivery member actuator.

7. The activation mechanism as claimed in claim 4, wherein the delivery member mechanism comprises a drum containing a drum torsion spring, wherein the first delivery member actuator is a drum insert body arranged in the drum, torsionally biased by the drum torsion spring, wherein the drum insert body comprises a protrusion extending axially from the drum, the protrusion being configured to interact with the second delivery member actuator when the first delivery member actuator is rotated.

8. The activation mechanism as claimed in claim 7, wherein the first delivery member actuator is provided with a radial blocking protrusion configured to bear against the locking member in the retracted position of the activation pin to thereby prevent rotation of the first delivery member actuator.

9. The activation mechanism as claimed in claim 8, wherein the drum is provided with an axial slit in which the radial blocking protrusion is configured to run when moved by the activation pin.

10. The activation mechanism as claimed in claim 1, wherein the activation button structure comprises an activation button and an activation button sleeve fixedly connected to the activation button, wherein the activation button sleeve is configured to receive the activation pin sleeve, wherein the activation pin sleeve is provided with radially inwards extending flexible arms configured to engage with the activation pin, wherein the activation button sleeve is configured to force the radially inwards extending flexible arms radially inwards to engage with the activation pin when the activation button structure is in the initial position, and wherein the activation button sleeve is configured to move axially relative to the activation pin sleeve when the activation button structure is moved towards the activation position enabling the radially inwards extending flexible arms to flex radially outwards thereby releasing the activation pin from engagement with the activation pin sleeve.

11. The activation mechanism as claimed in claim 1, wherein the activation pin has an electrically conducting surface.

12. An on-body medicament delivery device comprising:
    an outer housing, and
    the activation mechanism as claimed in claim 1 arranged in the outer housing,
    wherein the activation pin sleeve is fixed relative to the outer housing.

13. The on-body medicament delivery device as claimed in claim 12, comprising at least one electronic component and two contact elements that are spaced apart, wherein an electrically conducting surface of the activation pin is configured to provide an electrical connection between the two contact elements when the activation pin is in the extended position.

14. The on-body medicament delivery device as claimed in claim 12, comprising an inner housing provided with a first seal, wherein the activation pin is configured to pierce the first seal when the activation pin is moved from the retracted position towards the extended position.

15. An activation mechanism for an on-body medicament delivery device, wherein the activation mechanism comprises:
    a button configured to allow a user to move the button between an initial position and an activation position;
    a button sleeve slidably connected to the button such that movement of the button linearly slides the button sleeve relative to a pin sleeve fixed in relation to an outer housing of the on-body medicament delivery device; and
    an activation pin linearly movable relative to the pin sleeve from a retracted position to an extended position, where a resilient member biases the activation pin when in the retracted position,
    wherein linear movement in a first direction of the button from the initial position to the activation position causes the resilient member to linearly move the activation pin in a second direction that is opposite of the first direction.

16. The activation mechanism of claim 15, wherein the pin sleeve releasably locks the activation pin to prevent linear movement of the activation pin when the button is in the initial position.

17. The activation mechanism of claim 15 further comprising a delivery member configured to move tangentially relative to linear movement of the activation pin from an initial delivery member position to an administration position.

18. The activation mechanism of claim 17 further comprising a torsionally biased delivery member actuator operatively connected to the delivery member causing movement from the initial delivery member position to the administration position.

19. The activation mechanism of claim 17, wherein the linear movement of the activation pin causes linear movement of a locking member that releases a torsionally biased delivery member actuator that is operatively connected to the delivery member.

20. The activation mechanism of claim 15, wherein the pin sleeve comprises a flexible arm that is biased radially inward by the button sleeve when the button is in the initial position.

\* \* \* \* \*